(12) United States Patent
Higuchi et al.

(10) Patent No.: US 7,754,704 B2
(45) Date of Patent: *Jul. 13, 2010

(54) METHOD FOR TREATING HYPERGLYCEMIA

(75) Inventors: Ryuuichi Higuchi, Fukuoka (JP); Masanori Inagaki, Fukuoka (JP); Hirotoshi Hayasawa, Tokyo (JP); Muneo Yamada, Zama (JP); Miyuki Tanaka, Zama (JP); Eriko Misawa, Zama (JP); Noriko Wakimoto, Zama (JP); Yousuke Itou, Zama (JP)

(73) Assignee: Morinaga Milk Industry Co., Ltd., Minato-ku, Tokyo (JP)

( * ) Notice: Subject to any disclaimer, the term of this patent is extended or adjusted under 35 U.S.C. 154(b) by 1139 days.

This patent is subject to a terminal disclaimer.

(21) Appl. No.: 10/572,099

(22) PCT Filed: Mar. 30, 2005

(86) PCT No.: PCT/JP2005/006020

§ 371 (c)(1),
(2), (4) Date: Mar. 16, 2006

(87) PCT Pub. No.: WO2005/094838

PCT Pub. Date: Oct. 13, 2005

(65) Prior Publication Data

US 2007/0032463 A1 Feb. 8, 2007

(30) Foreign Application Priority Data

Mar. 31, 2004 (JP) ............................ 2004-103685
Apr. 6, 2004 (JP) ............................ 2004-112109

(51) Int. Cl.
*A61K 31/56* (2006.01)
(52) U.S. Cl. ...................................... 514/169; 514/182
(58) Field of Classification Search .................. 514/169, 514/182
See application file for complete search history.

(56) References Cited

U.S. PATENT DOCUMENTS

| 4,598,069 | A | 7/1986 | Hikino et al. | |
| 6,828,451 | B2 | 12/2004 | Barrault et al. | |
| 2003/0207818 | A1 | 11/2003 | Jia et al. | |
| 2008/0255077 | A1* | 10/2008 | Tanaka et al. | 514/182 |
| 2009/0004307 | A1* | 1/2009 | Tanaka et al. | 424/744 |
| 2009/0131388 | A1* | 5/2009 | Tanaka et al. | 514/182 |

FOREIGN PATENT DOCUMENTS

| JP | 60-214741 | 10/1985 | |
| JP | 01-312978 | 12/1989 | |
| JP | 05-247086 | 9/1993 | |
| JP | 08-208495 | 8/1996 | |
| JP | 09-040689 | 2/1997 | |
| JP | 09-059298 | 3/1997 | |
| JP | 09-224588 | 9/1997 | |
| JP | 10-036271 | 2/1998 | |
| JP | 10-036283 | 2/1998 | |
| JP | 10-045604 | 2/1998 | |
| JP | 10-120576 | 5/1998 | |
| JP | 10-215853 | 8/1998 | |
| JP | 10-330266 | 12/1998 | |
| JP | 11-511482 | 10/1999 | |
| JP | 2001-520019 | 10/2001 | |
| JP | 2002-205949 | 7/2002 | |
| JP | 2002-241293 | 8/2002 | |
| JP | 2002-371003 | 12/2002 | |
| JP | 2003-048837 | 2/2003 | |
| JP | 2003-095941 | 4/2003 | |
| JP | 2003-286185 | * | 10/2003 |
| WO | WO 97/16438 | 5/1997 | |
| WO | WO 99/19505 | 4/1999 | |
| WO | WO 02/05830 | 1/2002 | |
| WO | WO2004/067009 | * | 12/2004 |
| WO | WO2004/105770 | * | 12/2004 |

OTHER PUBLICATIONS

Waldemar Eichenberger and Birgit Urban, Sterols in Seeds and Leaves of Oats (Avena sativa L.), 3 Plant Cell Rep. 226 (1984).*
Seymour Bernstein and Everett Wallis, The Structure of B-Sitosterol, and its Preparation from Stigmasterol, 2 J. Org. Chem. 341, 342 (Sep. 1937).*
Miyuki Tanaka, et al, Identification of Five Phytosterols from Aloe Vera Gel as Anti-Diabetic Compounds, 29 Biol. Pharm. Bull. 1418 (2006).*
S. Yongchaiyudha, et al, Antidiabetic Activity of Aloe Vera L. Juice. I Clinical Trial in New Cases of Diabetes Mellitus, 3 Phytomedicine 241 (1996).*
Miyuki Tanaka, et al, Identification of Five Phytosterols from Aloe Vera Gel as Anti-Diabetic Compounds, 29 Biol. Pharm. Bull. 1418, 1420-21 (2006).*
Supplementary European Search Report dated Feb. 4, 2009 and issued to a counterpart European application.
Akihisa, et al. "Triterpene Alcohols and Sterols from the Fern *Gleichenia japonica* Spr.," Chem. Pharm. Bull., vol. 41, No. 3, pp. 624-626, 1993.
Bunyapraphatsara, et al. "Antidiabetic Activity of *Aloe vera* L. Juice II. Clinical Trial in Diabetes mellitus Patients in Combination with Glibenclamide," Phytomedicine, vol. 3, No. 3, pp. 245-248, 1996.
Okyar, et al. "Effect of *Aloe vera* Leaves on Blood Glucose Level in Type I and Type II Diabetic Rat Models," Phytotherapy Research, vol. 15, pp. 157-161, 2001.

(Continued)

Primary Examiner—Frederick Krass
Assistant Examiner—Sean Basquill
(74) Attorney, Agent, or Firm—Knobbe, Martens, Olson & Bear, LLP (57) ABSTRACT

A compound having a hyperglycemia improving effect and a hemoglobin A1c lowering action such as 4-methylcholest-7-en-3-ol, 4-methylergost-7-en-3-ol and 4-methylstigmast-7-en-3-ol is used as an active ingredient of a drug or food or drink for improving hyperglycemia.

1 Claim, 2 Drawing Sheets

OTHER PUBLICATIONS

Beppu, et al. "Hypoglycaemic and Antidiabetic Effects in Mice of *Aloe arborescens* Miller var. *natalensis* Berger," *Phytotherapy Research*, vol. 7, pp. S37-S42, 1993.

Nippon Rinsho, No. 748, vol. 1, pp. 615-617, 1999 with a partial English translation.

Nippon Rinsho, No. 808, vol. 2, pp. 405-409, 2002 with a partial English translation.

Yazaki Y. & Muramatsu M. Ed., "Front Line of Diabetes mellitus," pp. 126-139, Yodosha, 1997 with a partial English translation.

Yamada, et al. "Experimental methods of Biochemistry," vol. 24, *Experimental Methods for Fat and Lipid Metabolism*, pp. 174-175, Gakkai Shuppan Center, 1989 with an English abstract.

Yongchaiyudha, et al. "Antidiabetic Activity of *Aloe vera* L. Juice.I. Clinical Trial in New Cases of Diabetes mellitus," *Phytomedicine*, vol. 3, No. 3, pp. 241-243, 1996.

Koo, "Aloe Vera, Antiulcer and Antidiabetic Effects," *Phytotherapy Research*, vol. 8, pp. 461-464, 1994.

Akihisa T., Matsumoto T., *Yukagaku*, vol. 36, pp. 301-319, 1987 with a relevance explanation.

Can, et al. "Effect of *Aloe vera* Leaf Gel and Pulp Extracts on the Liver in Type-II Diabetic Rat Models," *Biol. Pharm. Bull*. vol. 27, No. 5, pp. 694-698, 2004.

Afzal, et al. "Identification of Some Prostanoids in *Aloe vera* Extracts," *Planta Med.*, vol. 57, pp. 38-40, 1991.

Ghannam, et al. "The Antidiabetic Activity of Aloes: Preliminary Clinical and Experimental Observations," *Hormone Res.*, vol. 24, pp. 288-294, 1986.

Ajabnoor, "Effects of Aloes on Blood Glucose Levels in Normal and Alloxan Diabetic Mice," *Journal of Ethnopharmacology*, vol. 28 pp. 215-220, 1990.

Grover, et al. "Medicinal Plants of India with Anti-Diabetic Potential," *Journal of Ethnopharmacology*, vol. 81, pp. 81-100, 2002.

Bolkent, et al. "Effect of *Aloe vera* (L.) Burm. fil. Leaf Gel and Pulp Extracts on Kidney in Type-II Diabetic Rat Models," *Indian Journal of Experimental Biology*, vol. 42, pp. 48-52, Jan. 2004.

Hikino, et al. "Isolation and Hypoglycemic Activity of Arborans A and B, Glycans of *Aloe arborescens var. natalensis* Leaves," *Int. J. Crude Drug Res.*, vol. 24, pp. 183-186, 1986.

Rajasekaran, et al. "Hypoglycemic Effect of *Aloe vera* Gel on Streptozotocin-Induced Diabetes in Experimental Rats," *Journal of Medicinal Food*, vol. 7, No. 1, pp. 61-66, 2004.

САНДЕР., "Технология ИОборудование Галеновых Лроизводств" МЕДГИЗЬ, p. 162, 1956.

Office Action dated Mar. 13, 2007 and issued to a corresponding Russian Federation patent application. A translation of the Office Action is provided.

Notice of Reason for Rejection issued in a related Japanese application.

Abou Zeid, "Chemical and Biological Study of Leaves of some *Musa* Species," *Egypt. J. Pharm. Sci.*, No. 39, Nos. 4-6, pp. 379-398, 1998.

Miettinen, et al. "Low Synthesis and High Absorption of Cholesterol Characterize Type 1 Diabetes," *Diabetes Care*, vol. 27, No. 1, pp. 53-58, Jan. 2004.

Yeh, et al. "Systematic Review of Herbs and Dietary Supplements for Glycemic Control in Diabetes," *Diabetes Care*, vol. 26, No. 4, pp. 1277-1294, Apr. 2003.

International Search Report completed Jun. 22, 2005.

Jamaluddin, et al. Hypoglycaemic Effect of Stigmast-4-en-3-one, from *Parkia speciosa* Empty Pods, 'Food Chemistry, vol. 54, No. 1, pp. 9-13, 1995.

Tanaka, et al. "Identification of Five Phytosterols from Aloe Vera Gel as Anti-diabetic Compounds," *Biological and Pharmaceutical Bulletin*, vol. 29, No. 7, pp. 1418-1422, 2006.

\* cited by examiner

METHOD FOR TREATING HYPERGLYCEMIA

RELATED APPLICATIONS

This application is the U.S. National Phase under 35 U.S.C. §371 of International Application PCT/JP2005/006020, filed Mar. 30, 2005, which was published in a language other than English, which claims priority to JP 2004-103685, filed Mar. 31, 2004 and JP 2004-112109, filed Apr. 6, 2004.

TECHNICAL FIELD

The present invention relates to a drug and food or drink for improving hyperglycemia, which contains a compound that can be safely ingested without causing acute hypoglycemia and has a long-term blood glucose level control action lowering the hemoglobin A1c level.

BACKGROUND ART

Hemoglobin A1c, a binding product of glucose and hemoglobin, increases depending on the severity of hyperglycemia in a glucose level-dependent manner. Because hemoglobin A1c once produced is not eliminated until the lifetime of erythrocyte (120 days) runs out, it reflects the past blood glucose control conditions over a long period of time (Non-patent document 1). Hemoglobin A1c was adopted as a selected test item of the basic health screening according to the Health Law for the Aged since 1996 and adopted as an auxiliary diagnosis indicator of diabetes mellitus in the new diagnosis criteria of diabetes mellitus in 1999. Therefore, it is considered that hemoglobin A1c is an indicator of great clinical significance (Non-patent document 2).

If a hyperglycemic condition is sustained, glucose specific insulin hyposecretion and insulin resistance are observed and serve as factors that further aggravate hyperglycemia (Non-patent document 3). Because long-term blood glucose level control is necessary to prevent progression from the hyperglycemic condition to onset of diabetes mellitus, it is considered to become necessary to suppress increase in the hemoglobin A1c level. Alimentotherapies and exercise are recommended to control blood glucose level in patients with prediabetes (condition suspected of diabetes). Although various functional foods for preventing postprandial increases in blood glucose level (food for specified health uses) have already been marketed, all of these only have a temporary effect of suppressing increase in blood glucose level. Therefore, control of blood glucose level over a long period of time cannot be expected, and development of such a substance having a hemoglobin A1c level lowering action has been desired.

Furthermore, α-glucosidase inhibitors, sulfonylurea drugs as insulin secretagogues, thiazolidine derivatives as insulin resistance improving agents and so forth are currently used as therapeutic agents for diabetes mellitus. However, the drug efficacies thereof are not satisfactory, and they suffer many problems such as side effects causing coma due to rapid drop in blood glucose level.

Under the aforementioned circumstances, discovery of a substance that can be safely ingested without causing hypoglycemia and has a long-term blood glucose level control action by decreasing the hemoglobin A1c level has been strongly desired.

Conventionally, as examples of substances having an effect of suppressing increases in blood glucose level, the prior art references have disclosed a hyperglycemia suppressing agent containing a banaba-derived ingredient (Patent document 1), a hyperglycemia suppressing agent containing a concentrated extract of fermentation product of wheats or barleys as an active ingredient (Patent document 2) and so forth.

Furthermore, as techniques of using a triterpene glycoside as an active ingredient, for example, a diabetes preventing agent containing a glycoside extracted from *Gymnema inodorum* as an active ingredient (Patent document 3), a metabolism improving method and a composition therefor containing corosolic acid extracted from banaba as an active ingredient (Patent document 4), a lipase inhibitor (Patent document 5) and a triterpene derivative having an immunosuppressing activity (Patent document 6) have been disclosed.

Furthermore, it has been disclosed that the insulin action enhancing activity of a compound having a lanostane skeleton or 3,4-secolanostane skeleton (Patent document 7) enhances the insulin action in regulation of adipocyte differentiation, although the effect thereof on diseases in the pancreas is unknown.

Furthermore, compounds selected from the group consisting of 24-alkylcholesten-3-ones and 24-alkylcholestan-3-ones that have no double bond in the basic steroid skeleton have been disclosed as hypoglycemic agents (Patent document 8).

Meanwhile, lophenol (one of the stereoisomers of 4-methylcholest-7-en-3-ol) has been known to be an intermediate of the biosynthetic pathway starting from squalane in plants (Non-patent document 4). As for prior arts of this compound, however, there is only a reference concerning the biosynthetic system of lophenol (Non-patent document 5), and the use of the compound is not known at all.

The genus *Aloe* in the family Liliaceae is a group of plants including *Aloe vera* (*Aloe barbadensis* Miller) and *Aloe arborescens* (*Aloe arborescens* Miller var. *natalensis* Berger) and so forth, and they are empirically known to have various efficacies. The prior arts regarding the use of plants of the genus *Aloe* include immunomodulating polysaccharides (Patent document 9), immunosuppression improving agents containing a butanol fraction of an aloe extract or aloin (Patent document 10), HSP60 family protein synthesis suppressing agents containing aloin derivatives (Patent documents 11 to 13), protein having lectin activity derived from aloe leaf-skin (Patent document 14) and so forth.

As the prior arts regarding improvement of blood glucose levels by the plants of the genus *Aloe*, clinical studies in the United States (Non-patent document 6) and a hypoglycemic action observed in animal studies (Non-patent documents 7 and 8) and polysaccharides in plants of the genus *Aloe* (Patent document 15) have been disclosed. In these prior arts, the hypoglycemic ingredients of the plants of the genus *Aloe* were predicted to be polysaccharides or glycoproteins. Furthermore, it has been disclosed that, in a pressed extract of *Aloe vera* and a hypoglycemic agent containing the extract as an active ingredient (Patent document 16), a characteristic peak unique to an ester group observed in the FT-IR chart correlates with the activity, that the active ingredient is a polysaccharide, amino acid, malic acid or the like, and that the aforementioned active ingredient is degraded in commercially available *Aloe vera* gel powders, *Aloe vera* gel solutions and *Aloe vera* gel extracts. Furthermore, in addition to the above, a hypoglycemic action of aloe polysaccharides (Patent document 17) and antioxidative action of 7-hydroxychromone contained in aloe (Patent document 18) have been disclosed.

[Patent document 1] Japanese Patent Laid-open (Kokai) No. 2003-095941
[Patent document 2] Japanese Patent Laid-open No. 2002-371003
[Patent document 3] Japanese Patent Laid-open No. 05-247086
[Patent document 4] Japanese Patent Laid-open No. 2002-205949
[Patent document 5] Japanese Patent Laid-open No. 09-040689
[Patent document 6] International Patent Unexamined Publication in Japanese (Kohyo) No. 11-511482
[Patent document 7] Japanese Patent Laid-open No. 10-330266
[Patent document 8] Japanese Patent Laid-open No. 2003-048837
[Patent document 9] International Patent Application Unexamined Publication in Japanese No. 2001-520019
[Patent document 10] Japanese Patent Laid-open No. 08-208495
[Patent document 11] Japanese Patent Laid-open No. 10-120576
[Patent document 12] Japanese Patent Laid-open No. 10-045604
[Patent document 13] Japanese Patent Laid-open No. 10-036271
[Patent document 14] Japanese Patent Laid-open No. 09-059298
[Patent document 15] Japanese Patent Laid-open No. 60-214741
[Patent document 16] Japanese Patent Laid-open No. 2003-286185
[Patent document 17] U.S. Pat. No. 4,598,069
[Patent document 18] U.S. Patent Application Publication No. 2003/0207818
[Non-patent document 1] Nippon Rinsho, No. 748, Vol. 1, pp. 615-617, 1999
[Non-patent document 2] Nippon Rinsho, No. 808, Vol. 2, pp. 405-409, 2002
[Non-patent document 3] Yazaki Y. & Muramatsu M. Ed., "Front Line of Diabetes Mellitus," pp. 126-139, Yodosha, 1997
[Non-patent document 4] Yamada A., "Experimental Methods of Biochemistry", Vol. 24, Experimental Methods for Fat and Lipid Metabolism, p. 174, Gakkai Shuppan Center, 1989
[Non-patent document 5] Chem. Pharm. Bull., pp. 624-626, 1993
[Non-patent document 6] Phytomedicine, Vol. 3, pp. 245-248, 1996
[Non-patent document 7] Phytotherapy Research, Vol. 15, pp. 157-161, 2001
[Non-patent document 8] Phytotherapy Research, Vol. 7, pp. 37-42, 1993

DISCLOSURE OF THE INVENTION

An object of the present invention is to provide a drug and food or drink for improving hyperglycemia, which contains a compound that can be safely ingested without causing acute hypoglycemia and has a long-term blood glucose level control action lowering the hemoglobin A1c level.

The inventors of the present invention assiduously studied in order to achieve the foregoing object. As a result, they found that a compound having a structure similar to that of lophenol contained in a wide range of plants could be safely ingested without causing acute hypoglycemia and had a long-term blood glucose level control action lowering the hemoglobin A1c level. The present invention was accomplished on the basis of the above finding.

That is, the present invention provides a drug and food or drink for improving hyperglycemia, which contains a compound represented by the following general formula (1) as an active ingredient:

In the formula, R1 represents a straight or branched alkyl group having 6 to 16 carbon atoms, which may contain no double bond or 1 or 2 double bonds and may contain a hydroxyl group and/or a carbonyl group, R2 and R3 each independently represent a hydrogen atom, an alkyl group having 1 to 3 carbon atoms or a substituted alkyl group having 1 to 3 carbon atoms, and R4 forms C=O with the carbon atom constituting the ring or represents —OH or —OCOCH$_3$.

According to a preferred embodiment, one of R2 and R3 is a hydrogen atom, the other is methyl group, and R4 is a hydroxyl group.

Further, according to a preferred embodiment, in the aforementioned drug and food or drink, R1 is represented by any one of the following formulae:

—CH$_2$—CH$_2$—CH(—CH$_2$—CH$_3$)—CH(CH$_3$)$_2$

—CH$_2$—CH$_2$—CH=C(CH$_3$)$_2$

—CH$_2$—CH=C(CH$_3$)—CH(CH$_3$)$_2$

—CH$_2$—CH$_2$—C(=CH—CH$_3$)—CH(CH$_3$)$_2$

—CH$_2$—CH$_2$—CH(Ra)=C(CH$_3$)Rb (wherein Ra and Rb is any of —H, —OH, or —CH$_3$)

—CH$_2$—CH$_2$—CH(Rc)-CH(CH$_3$)Rd (wherein Rc and Rd is any of —H, —OH, or —CH$_3$)

Furthermore, according to a preferred embodiment, the aforementioned compound contained in the aforementioned drug and food or drink is selected from the group consisting of 4-methylcholest-7-en-3-ol, 4-methylergost-7-en-3-ol and 4-methylstigmast-7-en-3-ol.

Further, according to a preferred embodiment, the aforementioned drug contains 0.001 to 10% by dry mass of the aforementioned compound.

Further, according to a preferred embodiment, the aforementioned food or drink contains 0.0001 to 1% by dry mass of the aforementioned compound.

The present invention further provides a drug for improving hyperglycemia, which contains a composition consisting of an organic solvent extract or hot water extract of a plant or a fraction thereof containing a compound represented by the aforementioned general formula (1) and containing 0.001 to 10% by dry mass of the aforementioned compound as an active ingredient, or food or drink for improving hyperglycemia, which contains a composition containing 0.0001 to 1% by dry mass of the aforementioned compound as an active ingredient.

The aforementioned plant used for the aforementioned drug and food or drink is preferably a plant of the family Lillaceae, and according to a particularly preferred embodiment, the aforementioned plant of the family Liliaceae is a plant classified into the genus *Aloe*.

The present invention provides the aforementioned food or drink having a hyperglycemia improving effect and attached with an indication that it is used for improvement of hyperglycemia.

Hereafter, the aforementioned drug and food or drink are also generically referred to as "the drug or food or drink of the present invention."

The present invention further provides use of a compound represented by the aforementioned general formula (1) or a composition containing the same for the production of a drug for improving hyperglycemia. According to a preferred embodiment of the use of the present invention, 0.001 to 10% by dry mass or more of the aforementioned compound is contained.

The present invention further provides a method for improving hyperglycemia, which comprises administering a compound represented by the aforementioned chemical formula (1) or a composition containing the same to a subject whose hyperglycemia is to be improved. According to a preferred embodiment of the method of the present invention, the aforementioned composition contains 0.001 to 10% by dry mass or more of the aforementioned compound.

BEST MODE FOR CARRYING OUT THE INVENTION

Hereafter, preferred embodiments of the present invention will be explained in detail. However, the present invention is not limited to the following preferred embodiments, and the preferred embodiments can be freely modified within the scope of the present invention.

According to an embodiment, the drug or food or drink of the present invention contains a compound represented by the aforementioned general formula (1) and having a hyperglycemia improving effect and a hemoglobin A1c lowering action (hereinafter also be referred to as "the compound of the present invention") as an active ingredient. According to another embodiment, the drug or food or drink of the present invention comprises a composition containing an organic solvent extract or a hot water extract of a plant or a fraction thereof containing the compound of the present invention as an active ingredient.

In the aforementioned general formula (1), it is preferred that R1 represents a straight or branched alkyl group having 6 to 16 carbon atoms, which may contain no double bond or 1 or 2 double bonds, R2 and R3 each independently represent a hydrogen atom, an alkyl group having 1 to 3 carbon atoms or a substituted alkyl group having 1 to 3 carbon atoms, and R4 forms C=O with the carbon atom constituting the ring or represents —OH or —OCOCH$_3$. As the aforementioned alkyl group having 1 to 3 carbon atoms, methyl group, ethyl group and so forth are preferred, and methyl group is particularly preferred.

The aforementioned R1 is preferably any one of the groups represented by the following formulae:

(wherein Ra and Rb is any of —H, —OH, or —CH$_3$)

(wherein Rc and Rd is any of —H, —OH, or —CH$_3$)

Further, it is preferred that one of R2 or R3 is a hydrogen atom, and the other is a methyl group. Further, it is preferred that R4 is a hydroxyl group.

The most preferred compounds as the aforementioned compound are those represented by the following formulae, 4-methylcholest-7-en-3-ol (formula (2)), 4-methylergost-7-en-3-ol (formula (3)) and 4-methylstigmast-7-en-3-ol (formula (4)).

(2)

(3)

(4)

That is, 4-methylcholest-7-en-3-ol is a compound represented by the aforementioned general formula (1) wherein one of R2 and R3 is a hydrogen atom, the other is methyl group, R4 is a hydroxyl group, and R1 is a group represented by the aforementioned formula (vi) (Rc represents —H, and Rd represents —CH$_3$). Further, 4-methylergost-7-en-3-ol is a compound represented by the aforementioned general formula (1) wherein one of R2 and R3 is a hydrogen atom, the other is methyl group, R4 is a hydroxyl group, and R1 is a group represented by the aforementioned formula (vi) (Rc and Rd both represent —CH$_3$). Further, 4-methylstigmast-7-en-3-ol is a compound represented by the aforementioned general formula (1) wherein one of R2 and R3 is a hydrogen atom, the other is methyl group, R4 is a hydroxyl group, and R1 is a group represented by the aforementioned formula (i).

The drug or food or drink of the present invention may contain one type or two or more arbitrary types of the aforementioned compounds.

It is known that lophenol is contained in plants, and the compound of the present invention can be produced according to the known method for producing lophenol (Yamada A., "Experimental Methods of Biochemistry", Vol. 24, Experimental Methods for Fat and Lipid Metabolism, p. 174, Gakkai Shuppan Center, 1989). The compound of the present invention can be obtained by, for example, extracting the compound from a plant containing the same using a method such as extraction with an organic solvent or extraction with hot water and purifying the obtained extract. In the present invention, although the compound of the present invention may be purified, a composition such as a plant extract or a fraction thereof may also be used so long as it contains an effective amount of the compounds.

Examples of the aforementioned plant include a plant belonging to the family Liliaceae. Examples of the plant belonging to the family Liliaceae include plants belonging to the genus *Aloe* or *Allium*. Examples of the plants of the genus *Aloe* include *Aloe vera* (*Aloe barbadensis Miller*), *Aloe ferox Miller, Aloe africana Miller, Aloe arborescen Miller* var. *natalensis Berger, Aloe spicata Baker* and so forth. In the production of the compound of the present invention or a composition containing the same, although the whole of the aforementioned plant may be used, it is preferable to use mesophyll (clear gel portion) thereof. Such a plant or a part thereof is disrupted preferably by using a homogenizer or the like and thereby liquefied, and the disruption product is extracted by using an organic solvent or hot water. Examples of the organic solvent include alcohols such as methanol, ethanol and butanol; esters such as methyl acetate, ethyl acetate, propyl acetate and butyl acetate; ketones such as acetone and methyl isobutyl ketone; ethers such as diethyl ether and petroleum ether; hydrocarbons such as hexane, cyclohexane, toluene and benzene; halogenated hydrocarbons such as carbon tetrachloride, dichloromethane and chloroform; heterocyclic compounds such as pyridine; glycols such as ethylene glycol; polyhydric alcohols such as polyethylene glycol; nitrile solvents such as acetonitrile, mixtures of these solvents and so forth. Further, these solvents may be anhydrous or hydrous. Among these solvents, ethyl acetate/butanol mixture (3:1) and chloroform/methanol mixture (2:1) are particularly preferred.

As the extraction method, a method used for usual extraction of a plant component can be used. Usually used is, for example, a method of refluxing 1 to 300 parts by mass of an organic solvent with 1 part by mass of fresh plant or dried plant with heating at a temperature below the boiling point of the solvent and stirring or shaking, or a method of performing extraction by ultrasonication at room temperature. By isolating insoluble matters from the extraction liquor using a suitable method such as filtration or centrifugation, a crude extract can be obtained.

The crude extract can be purified by various types of chromatography such as normal or reverse phase silica gel column chromatography. When a gradient of chloroform/methanol mixture is used in normal phase silica gel column chromatography as an elution solvent, the compound of the present invention is eluted with a mixing ratio of chloroform:methanol=about 25:1. Further, when a hexane/ethyl acetate mixture (4:1) is used in reverse phase silica gel column chromatography as an elution solvent, the compound of the present invention is eluted in a fraction eluted at an early stage.

The obtained fraction can be further purified by HPLC or the like.

Further, the compound used for the present invention may also be produced by a chemical synthesis method or a biological or enzymatic method using microorganisms, enzymes or the like.

Whether a compound or a composition containing the same obtained as described above is or contains the compound of the present invention can be confirmed by, for example, mass spectrometry (MS), nuclear magnetic resonance (NMR) spectroscopy or the like.

The compound of the present invention has an action of lowering the hemoglobin A1c level, and as a result, it can control the blood glucose level over a long period of time. Therefore, it can be used as an active ingredient of a hyperglycemia improving agent.

Furthermore, because leaf-skin of *Aloe vera* contains barbaloin and aloe-emodin having a laxative action, it is conventionally considered to be unfavorable as a drug or food or drink for which laxative action is not expected. Therefore, it is preferred that the composition containing the compound of the present invention does not contain these ingredients. Further, mesophyll of *Aloe vera* and a disruption product thereof may also be used as an active ingredient of a hyperglycemia improving agent.

The compound of the present invention can be used as an active ingredient of the drug or food or drink of the present invention as it is. Further, an organic solvent extract or a hot water extract of a plant or a fraction thereof containing the compound of the present invention (hereinafter referred to as "extract etc.") may also be used as an active ingredient of the drug or food or drink. In this case, the aforementioned extract etc. to be contained in the drug preferably contains 0.001 to 10% by dry mass, more preferably 0.01 to 1% by dry mass, particularly preferably 0.05 to 1% by dry mass, of the compound of the present invention. Further, the aforementioned extract etc. to be contained in the food or drink preferably contains 0.0001 to 1% by dry mass, more preferably 0.001 to 1% by dry mass, particularly preferably 0.005 to 1% by dry mass, of the compound of the present invention. The aforementioned extract etc. may contain 2 or more types of the compound of the present invention. Further, the aforementioned extract etc. may be a solution, or can also be lyophilized or spray-dried in a conventional manner and stored or used as powder.

As the drug of the present invention, the compound of the present invention or a composition containing the same per se, or the compound of the present invention or a composition containing the same combined with a pharmaceutically acceptable carrier can be orally or parenterally administered to a mammal including human. In the drug of the present invention, the compound of the present invention may be a pharmaceutically acceptable salt. Examples of the pharmaceutically acceptable salt include both metal salts (inorganic salts) and organic salts including, for example, those listed in "Remington's Pharmaceutical Sciences," 17th edition, p. 1418, 1985. Specific examples thereof include, but not limited to, inorganic acid salts such as hydrochloride, sulfate, phosphate, diphosphate, hydrobromate and sulfate, and organic acid salts such as malate, maleate, fumarate, tartarate, succinate, citrate, acetate, lactate, methanesulfonate, p-toluenesulfonate, pamoate, salicylate and stearate. Furthermore, the salt may be a salt with a metal such as sodium, potassium, calcium, magnesium and aluminum or a salt with an amino acid such as lysine. Furthermore, solvates such as hydrates of the aforementioned compound or pharmaceutically acceptable salts thereof also fall within the scope of the present invention.

Dosage form of the drug of the present invention is not particularly limited and can be suitably selected depending on the therapeutic purpose. Specific examples thereof include tablet, pill, powder, solution, suspension, emulsion, granules, capsule, syrup, suppository, injection, ointment, patch, eye drop, nasal drop and so forth. For the preparation, additives generally used in usual hyperglycemia improving drugs as pharmaceutical carriers such as excipients, binders, disintegrating agents, lubricants, stabilizers, flavoring agents, diluents, surfactants and solvents for injection can be used. Furthermore, so long as the effect of the present invention is not degraded, the compound of the present invention or a composition containing the same can be used in combination with other drugs having a hyperglycemia improving effect.

Although the amount of the compound of the present invention or a composition containing the same contained in the drug of the present invention is not particularly limited and can be suitably selected, the amount in the pharmaceutical preparation may be, for example, 0.001 to 10% by mass, preferably 0.01 to 1% by mass, particularly preferably 0.05 to 1% by mass, in terms of the amount of the compound of the present invention.

The drug of the present invention is useful for a therapeutic or prophylactic treatment of a disease resulted from hyperglycemic conditions such as diabetes and its associated symptoms and conditions (likelihood of developing diabetes or related conditions). In particular, it can also be used to prevent onset of diabetes mellitus from hyperglycemic conditions. Furthermore, the drug of the present invention can cure or prevent various diseases, complications and so forth resulted from hyperglycemic conditions, and reduce risks of these diseases, complications and so forth.

Examples of such various diseases and complications resulted from hyperglycemic conditions include diabetic retinopathy, diabetic nephropathy, diabetic neuropathy, diabetic gangrene, cerebral apoplexy resulted from diabetes mellitus, myocardial infarction resulted from diabetes mellitus and so forth.

The term "hyperglycemic conditions" refers to conditions that the blood glucose levels are out of the normal ranges, and the normal ranges are generally defined as a fasting blood glucose level of 110 mg/dl or lower, a blood glucose level of 160 mg/dl or lower 1 hour after 75 g glucose load, and a blood glucose level of 120 mg/dl or lower 2 hours after the same glucose load (Nihon Rinsho, No. 806, Vol. 1, pp. 28-35, 2002). Furthermore, the drug of the present invention is preferably used for a treatment for a patient with a hemoglobin A1c level higher than normal, for example, a hemoglobin A1c level of 5.8% or higher.

The administration time of the drug of the present invention is not particularly limited and can be suitably selected according to the method for treating an objective disease. Furthermore, the administration route is preferably determined depending on the dosage form, age, sex and other conditions of patients, severity of symptoms of patients and so forth.

The dose of the active ingredient in the drug of the present invention is suitably selected depending on the dosing regimen, age, sex, severity of disease, other conditions of patients and so forth. The amount of the compound of the present invention as an active ingredient is usually selected from the range of, preferably 0.001 to 50 mg/kg/day, more preferably 0.01 to 1 mg/kg/day, as a tentative dose. Furthermore, when a composition containing the compound of the present invention is used, the dry weight of the composition is selected from the range of, preferably 0.1 to 1000 mg/kg/day, more preferably 1 to 100 mg/kg/day, as a tentative amount. In any case, the dose can be ingested, in a day, once or several times as divided portions.

The compound of the present invention or the extract etc. containing the same can be added to food or drink. The form and property of the food or drink are not particularly limited so long as the effect of the active ingredient is not degraded, and the food or drink can be orally ingested, and it can be produced in a conventional manner by using raw materials usually used for food or drink except that the aforementioned active ingredient is added.

The amount of the compound of the present invention or the extract etc. containing the same contained in the food or drink of the present invention is not particularly limited and can be suitably selected. For example, the compound of the present invention or the extract etc. containing the same is contained in food or drink in an amount of 0.0001 to 1% by mass, preferably 0.001 to 1% by mass, particularly preferably 0.005 to 1% by mass, in terms of the amount of the compound of the present invention.

The food or drink of the present invention can be used for various applications utilizing the hyperglycemia improving effect. For example, it can be used for applications as food or drink suitable for those who are getting concerned about their blood glucose levels, food or drink useful for decreasing or eliminating risk factors of lifestyle-related diseases such as diabetes mellitus, and so forth.

As for the food or drink of the present invention, the expression "improvement of hyperglycemia" means that improvement or prevention of various health damages resulted from hyperglycemia, and "prevention of hyperglycemia," "suppression of increase in blood glucose level," "improvement of increase in blood glucose level," "prevention of increase in blood glucose level," "improvement of high hemoglobin A1c level" and so forth are exemplified in the present invention as terms having a meaning similar to that of the aforementioned "improvement of hyperglycemia".

Furthermore, the food or drink of the present invention is useful for a prophylactic treatment of a disease resulted from hyperglycemic conditions such as diabetes and its associated symptoms and conditions (likelihood of developing diabetes or related conditions). In particular, it can also be used to prevent onset of diabetes from hyperglycemic conditions. Furthermore, the food or drink of the present invention can be used for a prophylactic treatment of various diseases, complications and so forth resulted from hyperglycemic conditions and can decrease risks of these diseases, complications and so forth.

Examples of such various diseases and complications resulted from hyperglycemic conditions include diabetic retinopathy, diabetic nephropathy, diabetic neuropathy, diabetic gangrene, cerebral apoplexy resulted from diabetes mellitus, myocardial infarction resulted from diabetes mellitus and so forth.

The food or drink of the present invention is preferably marketed as food or drink attached with an indication that the food or drink is used for improving hyperglycemia, for example, "food or drink containing a compound having hyperglycemia improving effect indicated as 'For improving hyperglycemia,'" "food or drink containing a plant extract indicated as 'For improving hyperglycemia,'" "food or drink containing *Aloe vera* extract indicated as 'For improving hyperglycemia'" and so forth.

Because the compound of the present invention and the extract etc. containing the same have a hyperglycemia improving effect, it is considered that the indication of "improvement of hyperglycemia" also means "suppression of increase in blood glucose level." Therefore, the food or drink of the present invention can be indicated as "For suppressing increase in blood glucose level." That is, the aforementioned indication of "For improvement of hyperglycemia" may be an indication of "For suppression of increase in blood glucose level."

The wording used for such an indication as mentioned above is not necessarily be limited to the expression "For improvement of hyperglycemia" or "For suppression of increase in blood glucose level", and any other wording expressing the effect of improving hyperglycemia or suppressing increase in blood glucose level of course falls within the scope of the present invention. As such a wording, for example, an indication based on various uses allowing consumers to recognize the effect of improving hyperglycemia or suppressing increase in blood glucose level is also possible. Examples include, for example, indications of "Suitable for those who are getting concerned with blood glucose levels", "Useful for decrease or elimination of risk factors (risks) of lifestyle-related diseases such as diabetes mellitus", and so forth.

The aforementioned term "indication" include all actions for informing consumers the aforementioned use, and any indications reminding or analogizing the aforementioned use fall within the scope of the "indication" of the present invention regardless of purpose, content, objective article, medium etc. of the indication. However, the indication is preferably made with an expression that allows consumers to directly recognize the aforementioned use. Specific examples include actions of indicating the aforementioned use on goods or packages of goods relating to the food or drink of the present invention, actions of assigning, delivering, displaying for the purpose of assigning or delivering or importing such goods or packages of goods indicated with the aforementioned use, displaying or distributing advertisements, price lists or business papers relating the goods with indicating the aforementioned use, or providing information including those as contents with indicating the aforementioned use by an electromagnetic method (Internet etc.) and so forth.

The indication is preferably an indication approved by the administration etc. (for example, an indication in a form based on an approval, which is qualified on the basis of any of various legal systems provided by the administration), and it is particularly preferably an indication on advertisement materials at the sales spots such as packages, containers, catalogs, pamphlets and POPS, others documents and so forth.

Examples of the indication further include, for example, indications as health food, functional food, enteric nutritive food, food for special dietary uses, food with nutrient function claims, quasi-drug and so forth as well as indications approved by the Ministry of Health, Labor and Welfare, for example, indications approved on the basis of the system of food for specified health uses and similar systems. Examples of the latter include indications as food for specified health uses, indications as food for specified health uses with qualified health claims, indications of influence on body structures and functions, indications of reduction of disease risk claims and so forth, and more precisely, typical examples include indications as food for specified health uses (especially indications of use for health) provided in the enforcement regulations of Health Promotion Law (Japan Ministry of Health, Labor and Welfare, Ministerial ordinance No. 86, Apr. 30, 2003) and similar indications.

EXAMPLES

The present invention will be explained more specifically with reference to the following examples. However, the scope of the present invention is not limited to the following examples.

Preparation Example 1

In an amount of 100 kg of mesophyll (clear gel portion) of *Aloe vera* was liquefied by using a homogenizer, added with 100 L of an ethyl acetate/butanol mixture (3:1) and stirred.

The mixture was left standing overnight, and then the ethyl acetate/butanol mixture and the aqueous layer were separated to recover the ethyl acetate/butanol mixture. The extract from this ethyl acetate/butanol mixture obtained by concentrating the ethyl acetate /butanol mixture under reduced pressure weighed 13.5 g. A solution of 13 g of this extract dissolved in 1 mL of a chloroform/methanol mixture (1:1) was loaded on a column filled with 400 g of Silica Gel 60 (Merck Ltd.) to attain adsorption of the components to the column, then the components were eluted with a chloroform/methanol mixture by the stepwise gradient method, in which the methanol concentration was increased stepwise (mixing ratios of chloroform:methanol=100:1, 25:1, 10:1, 5:1 and 1:1), and the eluate was fractionated for each mixing ratio of the aforementioned mixture. It was confirmed by normal phase and reverse phase thin layer chromatography (Merck Ltd., Silica Gel 60F254 and RP-18F2543) that, among these fractions, the compound of the present invention existed in the fraction eluted with the mixture of chloroform:methanol=25:1.

This crude purified substance (crude purification product 1) containing the compound of the present invention weighed 3 g. Further, the yields of the crude purification products obtained in the above operation from the fractions eluted with the mixtures of chloroform:methanol=10:1 and 1:1 were 1.17 and 2.27 g, respectively. The solvents of these fractions were removed, then each extract was dissolved in 1 mL of a chloroform/methanol mixture (1:1) and loaded on a column filled with 100 g of Silica Gel 60 to attain adsorption of the components to the column, and then the components were eluted with 1100 mL of a hexane/ethyl acetate mixture (4:1). The eluted fractions were collected as aliquots of 300 mL (fraction A), 300 mL (fraction B) and 500 mL (fraction C) in this order. The yields obtained after removing the solvents from the fractions A, B and C were 0.6 g, 1.35 g and 0.15 g, respectively.

It was confirmed by normal phase and reverse phase thin layer chromatography that the compound of the present invention had been concentrated in the fraction A (crude purification product 2). This crude purification product 2 was further separated by HPLC using COSMOSIL C18 (Nacalai Tesque, Inc.) with a chloroform/hexane mixture (85:15) to obtain 1.3 mg of compound 2 (4-methylcholest-7-en-3-ol), 1.2 mg of compound 3 (4-methylergost-7-en-3-ol) and 1 mg of compound 4 (4-methylstigmast-7-en-3-ol). The structures of these compounds were confirmed by MS and NMR.

Test Example 1

This test was performed in order to evaluate the hemoglobin A1c lowering action and the hyperglycemic condition improving effect of the compounds of the present invention.

(1) Preparation of Sample

The compound 2 (4-methylcholest-7-en-3-ol), compound 3 (4-methylergost-7-en-3-ol) and compound 4 (4-methylstigmast-7-en-3-ol) produced in Preparation Example 1 mentioned above were used as test samples 1, 2 and 3, respectively.

(2) Test Method

Six-week old male db/db mice (purchased from Clea Japan, Inc.) were used as type-II diabetes model mice. These mice were divided into groups, each consisting of 7 animals. Each test sample was dissolved in DMSO, and the concentration was adjusted to 1 µg/mL with physiological saline. The final DMSO concentration was adjusted to 0.2%. A solution that did not contain any of the test samples was used as a negative sample. The type-II diabetes model mice were orally administered with 1 mL of any of the test sample solutions once a day everyday with a sonde for 40 consecutive days. Further, β-sitosterol (Tama Biochemical Co., Ltd.) was administered to the model mice as a control sample 1. Fasting blood glucose levels and random blood glucose levels were measured over time by using Antsense II (Bayer-Sankyo Co., Ltd.). The fasting blood glucose levels were measured after 15 hours of fasting. Further, on the 35th day from the start of the administration, hemoglobin A1c levels were measured by using DCA 2000 (Bayer-Sankyo Co., Ltd.).

(3) Results (Blood Glucose Levels and Hemoglobin A1c Levels)

Figure 1:
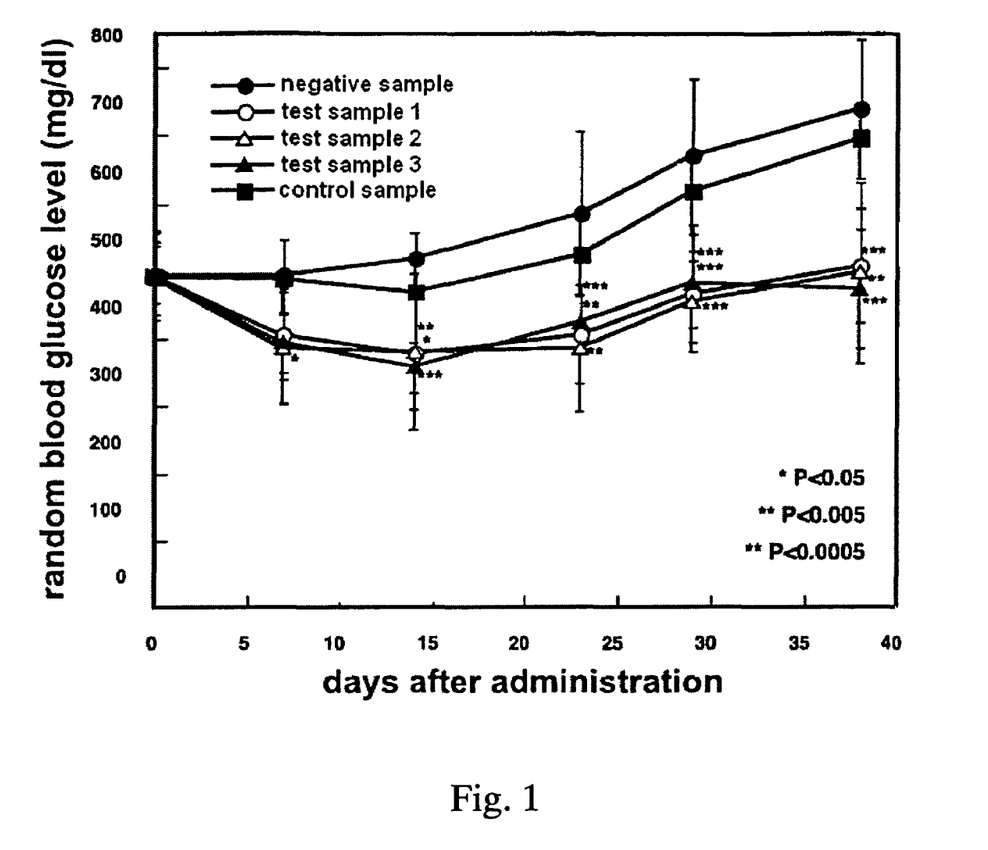
FIG. 1 is a graph showing changes over time in random blood glucose levels of mice administered with the compounds of the present invention.
Figure 2:
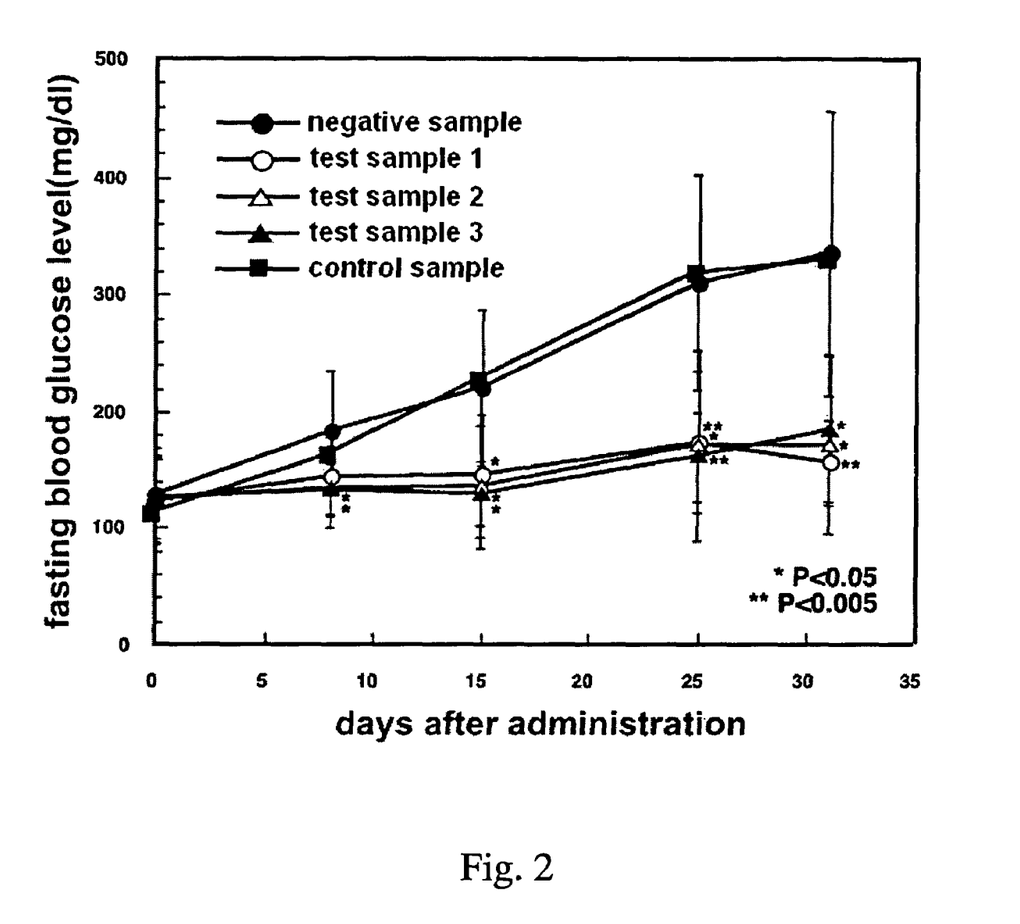
FIG. 2 is a graph showing changes over time in fasting blood glucose levels of mice administered with the compounds of the present invention.

Changes over time in random blood glucose levels and fasting blood glucose levels during the test sample administration period are shown in FIGS. 1 and 2. Whereas rapid increases were observed in both the random blood glucose levels and fasting blood glucose levels in the mice administered with the negative sample or the control sample 1, effect of suppressing the increase in blood glucose levels was clearly observed in the mice repeatedly administered with the test sample 1, 2 or 3.

The measurement results of hemoglobin A1c levels on the 35th day from the start of the administration are shown in Table 1. In comparison with the hemoglobin A1c levels after the administration of the negative sample, marked decreases of 15 to 26% were observed after the administration of either the test sample 1 or 2. In contrast, decreases of only about 0.5% were observed after the administration of the control sample 1, and thus almost no hemoglobin A1c lowering effect was observed. Further, there was no case showing acute hypoglycemic conditions during the administration period or after the administration, and no adverse side effect symptom was observed from viewpoints of body weight and pathological findings.

TABLE 1

| Samples | Hemoglobin A1c relative levels (%) 35th day from the administration | p value |
|---|---|---|
| test sample 1 | 80.2 ± 19.2 | 0.01 |
| test sample 2 | 82.7 ± 21.0 | 0.026 |
| test sample 3 | 77.8 ± 12.2 | 0.0015 |
| control sample 1 | 94.8 ± 8.5 | 0.314 |
| negative sample | 100 | |

Test Example 2

This test was performed in order to evaluate the hemoglobin A1c lowering action of the compounds of the present invention as well as an antidiabetic drug used in the clinical practice.

(1) Preparation of Sample

The compound 2 (4-methylcholest-7-en-3-ol), compound 3 (4-methylergost-7-en-3-ol) and compound 4 (4-methylstigmast-7-en-3-ol) produced in Preparation Example 1 mentioned above were used as test samples 1, 2 and 3.

(2) Test Method

Six-week old male db/db mice (purchased from Clea Japan, Inc.) were used as type-II diabetes model mice. These mice were divided into groups, each consisting of 7 animals. Each test sample was dissolved in DMSO, and the concentration was adjusted to 1 µg/mL with physiological saline. The final DMSO concentration was adjusted to 0.2%. A solution that did not contain any of the test samples was used as a negative sample. Further, as a control sample 2, ACTOS® tablets (Takeda Pharmaceutical Co., Ltd.) were ground in a mortar and dissolved in physiological saline so that the concentration of pioglitazone hydrochloride as the active ingredient should become 7.5 µg/mL. The type-II diabetes model mice were orally administered with 1 mL of each test sample solution, control sample 2 solution or negative sample solution once a day everyday with a sonde for 22 consecutive days. On the 23rd day from the start of the administration, hemoglobin A1c levels were measured by using DCA 2000 (Bayer-Sankyo Co., Ltd.).

(3) Results (Hemoglobin A1c Levels)

The measurement results of the hemoglobin A1c levels on the 23rd day from the start of the administration are shown in Table 2. In comparison with the hemoglobin A1c levels observed after the administration of the negative sample, statistically significant decreases of about 11% in the hemoglobin A1c levels were observed after the administration of either the test sample 1 or 2. In contrast, decrease of only about 0.8% was observed after the administration of the control sample 2, and no statistically significant effect was observed either. Further, there was no case showing acute hypoglycemic conditions during the administration period or after the administration, and no adverse side effect symptom was observed from viewpoints of body weight and pathological findings.

TABLE 2

| Samples | Hemoglobin A1c relative levels (%) 23th day from the administration | p value |
|---|---|---|
| test sample 1 | 89.9 ± 9.0 | 0.02 |
| test sample 2 | 91.0 ± 6.7 | 0.01 |
| test sample 3 | 88.8 ± 9.0 | 0.01 |
| control sample 2 | 92.1 ± 0.2 | 0.19 |
| negative sample | 100 | |

Test Example 3

This test was performed in order to evaluate the hemoglobin A1c lowering action of the crude purification product 2 containing the compounds of the present invention derived from *Aloe vera*.

(1) Preparation of Sample

The crude purification product 2 (fraction A) produced in Preparation Example 1 mentioned above was used as a test sample 4, and the fractions B and C were used as control samples 3 and 4, respectively.

(2) Test Method

Six-week old male db/db mice (purchased from Clea Japan, Inc.) were used as type-II diabetes model mice. These mice were divided into groups, each consisting of 7 animals. The test sample 4 and control samples 3 and 4 were each dissolved in DMSO, and the concentration was adjusted to 1 μg/mL with physiological saline. The final DMSO concentration was adjusted to 0.2%. A solution that did not contain the test sample was used as a negative sample. The type-II diabetes model mice were each orally administered with 1 mL of any of the sample solution 4, control samples 3 and 4 and negative sample once a day everyday with a sonde for 40 consecutive days. On the 35th day from the start of the administration, hemoglobin A1c levels were measured by using DCA 2000 (Bayer-Sankyo Co., Ltd.).

(3) Results (Hemoglobin A1c Levels)

The measurement results of the hemoglobin A1c levels on the 35th day from the start of the administration are shown in Table 3. In comparison with the hemoglobin A1c levels observed after the administration of the negative sample, marked decrease of 15% was observed after repetitive administration of the test sample 4. In contrast, decreases of only about 0.4 to 0.6% were observed after the administration of the control samples 3 and 4, and thus almost no hemoglobin A1c lowering effect was observed. Further, there was no case showing acute hypoglycemic conditions during the administration period or after the administration, and no adverse side reaction symptom was observed from viewpoints of body weight and pathological findings.

TABLE 3

| Samples | Hemoglobin A1c relative levels (%) 23th day from the administration | p value |
|---|---|---|
| test sample 4 (crude purification product 2) | 87.0 ± 5.0* | 0.0001 |
| control sample 3 | 94.0 ± 8.0 | 0.138 |
| control sample 4 | 96.0 ± 6.0 | 0.124 |
| negative sample | 100 | |

The drug and food or drink of the present invention can be safely administered or ingested without causing hypoglycemia and have a long-term blood glucose level control action lowering the hemoglobin A1c level. Further, the active ingredient of the drug and food or drink of the present invention can be produced from a plant that can be safely ingested from an experiential viewpoint for food and is readily available, for example, a plant of the family Liliaceae such as *Aloe vera* (*Aloe barbadensis Miller*).

What is claimed is:

1. A method for treating hyperglycemia, which comprises administering to a subject in need thereof a composition containing 0.001 to 10% by dry mass of a compound selected from the group consisting of 4-methylcholest-7-en-3-ol, 4-methylergost-7-en-3-ol, and 4-methylstigmast-7-en-3-ol.

* * * * *